United States Patent [19]
Tsitlik et al.

[11] Patent Number: 5,971,910
[45] Date of Patent: Oct. 26, 1999

[54] METHOD AND APPARATUS FOR ASSISTING A HEART TO PUMP BLOOD BY APPLYING SUBSTANTIALLY UNIFORM PRESSURE TO THE VENTRICLES

[75] Inventors: Joshua E. Tsitlik, Cliffside Park; Howard R. Levin, Teaneck, both of N.J.; Naum Ziselson, Baltimore, Md.; Paul C. Michelman, New York, N.Y.

[73] Assignee: Cardio Technologies, Inc., Pine Brook, N.J.

[21] Appl. No.: 08/997,052

[22] Filed: Oct. 17, 1997

Related U.S. Application Data

[60] Provisional application No. 60/048,156, May 30, 1997, and provisional application No. 60/028,722, Oct. 18, 1996.

[51] Int. Cl.$^6$ ........................................................ A61M 1/12
[52] U.S. Cl. ................................................... 600/16; 623/3
[58] Field of Search ............................... 601/153; 623/3; 600/16, 17

[56] References Cited

U.S. PATENT DOCUMENTS

| | | | |
|---|---|---|---|
| 3,613,672 | 10/1971 | Schiff | 600/16 |
| 4,192,293 | 3/1980 | Asrican | 600/16 |
| 4,690,134 | 9/1987 | Snyders | 600/16 |

FOREIGN PATENT DOCUMENTS

| | | |
|---|---|---|
| 1499158 | 7/1967 | France . |
| 457473 | 6/1973 | U.S.S.R. . |
| 984477 | 4/1981 | U.S.S.R. . |

Primary Examiner—William E. Kamm
Assistant Examiner—George R. Evanisko
Attorney, Agent, or Firm—Darby & Darby

[57] ABSTRACT

An apparatus and method for assisting a heart to pump blood includes a housing that defines an internal chamber for receiving a heart. The housing has a first opening to supply fluid to the internal chamber of the housing. Uniform pressure is applied to at least a majority portion of an exterior ventricular surface of a heart that is placed within the internal chamber so that the heart is substantially uniformly deformed to simulate a systolic phase.

36 Claims, 11 Drawing Sheets

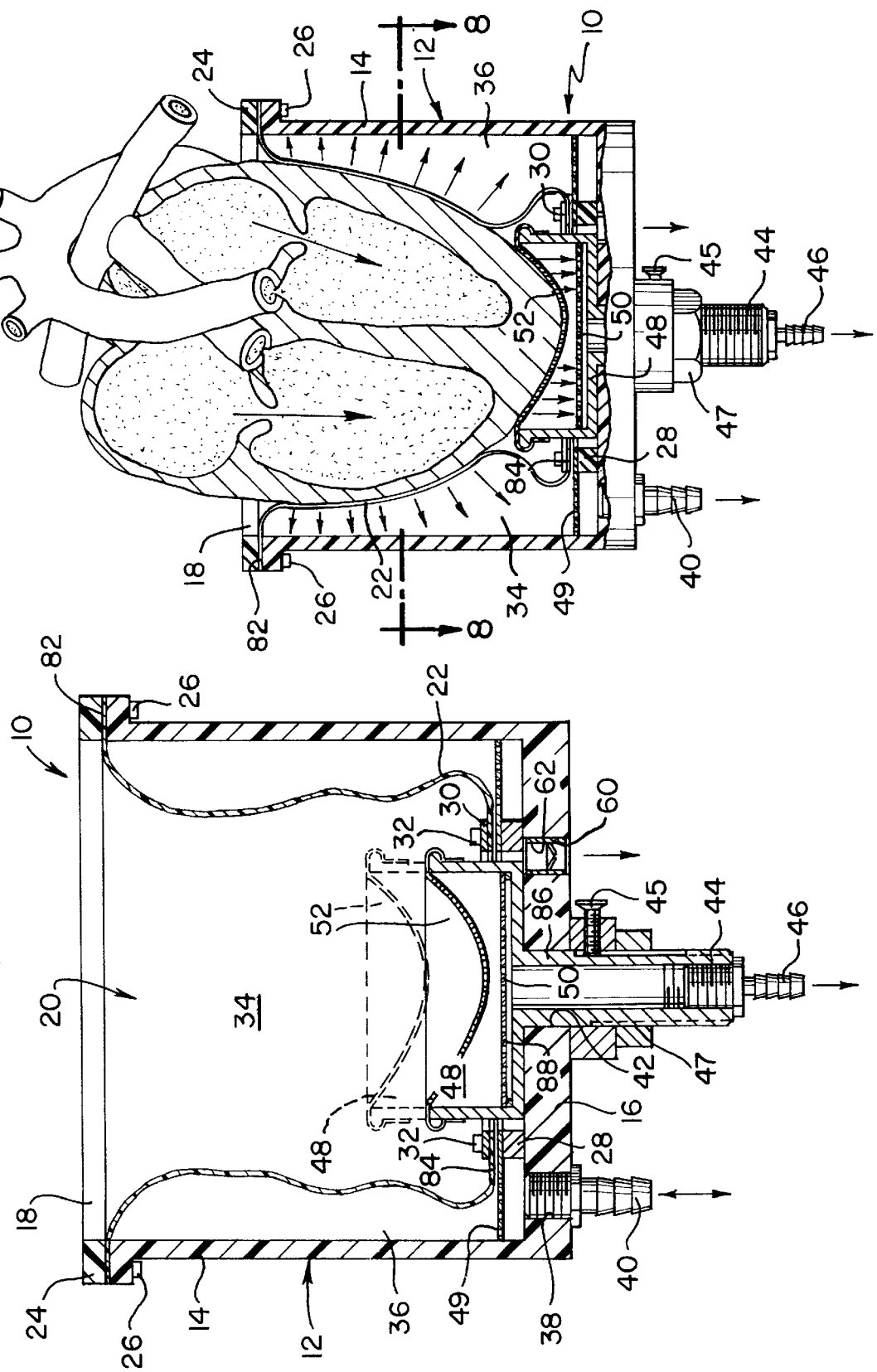

FIG. 14
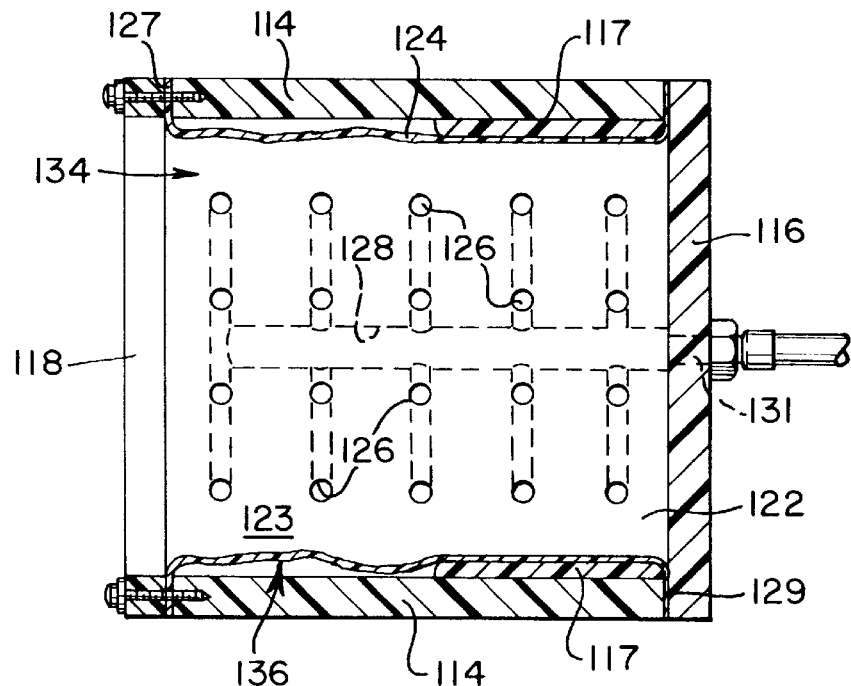
FIG. 15
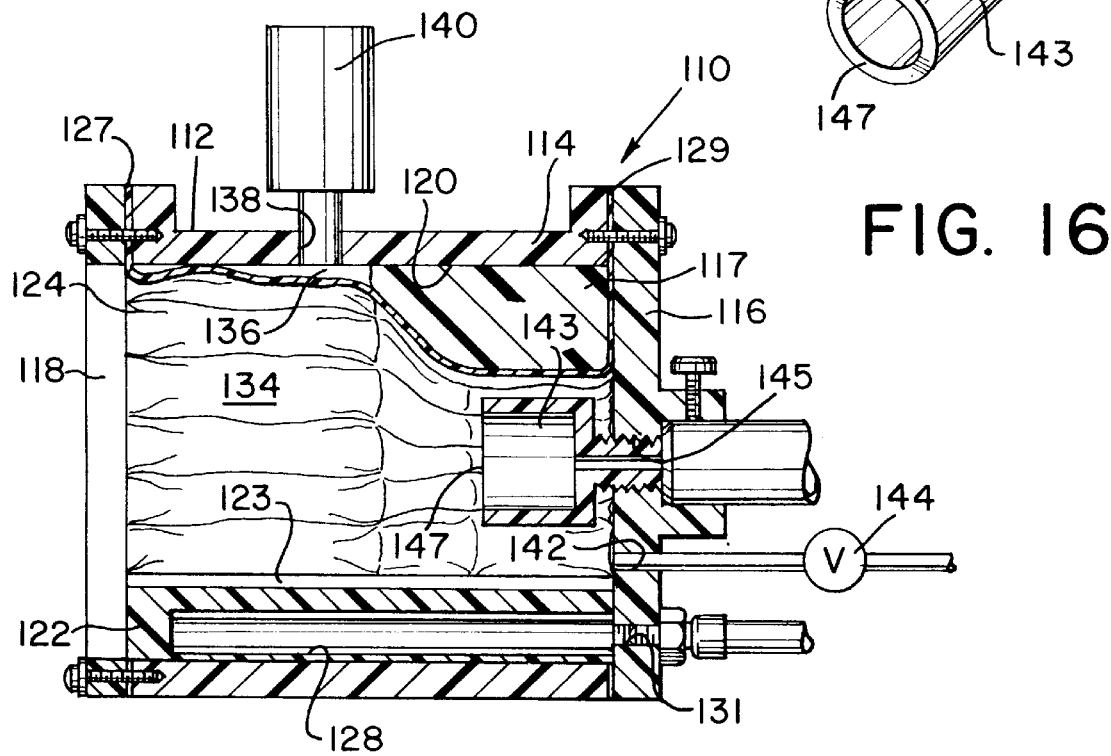
FIG. 16

METHOD AND APPARATUS FOR ASSISTING A HEART TO PUMP BLOOD BY APPLYING SUBSTANTIALLY UNIFORM PRESSURE TO THE VENTRICLES

This application claims benefit of Provisional Application Ser. No. 60/048,156 filed May 30, 1997, and claims benefit of Provisional Application Ser. No. 60/028,722 filed Oct. 18, 1996.

BACKGROUND OF THE INVENTION

1. Field of the Invention

The present invention relates to a method and apparatus for assisting a heart to pump blood by applying uniform pressure to at least a portion of the ventricular surface of the heart thereby causing the respective ventricle portion of the heart to be substantially uniformly deformed.

2. Discussion of the Related Art

Numerous attempts have been made to assist the heart by applying external pressure directly to the heart. One such example is direct manual compression of the heart by a person's hand during open chest cardiopulmonary resuscitation. Often, however, it may be advantageous for the patient if cardiac or circulatory support is performed by compressing the heart for extended periods of time, such as hours, days or weeks, and it is quite difficult for medical personnel to apply a rhythmic pulsating pressure for an extended period of time. Further, it is impossible to apply by hand a uniform compressing force to a majority portion of the exterior ventricle surface of the chamber of the heart.

To overcome this problem, mechanical devices have been developed to apply external pressure directly to the heart. These devices utilize an inflatable liner that surrounds the heart. For example, U.S. Pat. Nos. 3,455,298 and 5,119,804, both to Anstadt, disclose a cup that is provided with an elastomeric liner. The heart is held in place within the liner, which is cyclically inflated and deflated to apply external pressure to the heart. While this device provided an improvement in hemodynamics, it has several disadvantages.

One disadvantage is that only a fraction of the external fluid pressure that is applied in the cup inlet to displace the liner, which in turn displaces the heart wall, is transmitted to supplement the internal pressure of the heart and is used to pump blood. As the liner is inflated and stretched, a transmural pressure is created in the liner. The transmural pressure in the liner is the difference in pressure that is applied to both sides of the liner. In other words, the transmural pressure is the pressure within the liner that is generated by the elastic wall tensions of the liner. Referring now to FIG. 11, and as described in *Augmentation of Pressure In A Vessel Indenting the Surface of the Lung,* 1987, by Joshua E. Tsitlik, et al. the transmural pressure ($P_{tm}$) for a stretched liner is:

$$P_{tm}=P_{in}-P_{out}=T_1/R_1+T_2/R_2$$

Where the radii $R_1$ and $R_2$ are the maximum and the minimum radii of the membrane curvature, respectively, i.e., the principal radii of curvature. The vectors $T_1$ and $T_2$ are the elastic wall tensions (the force per unit length) acting along the edges of the surface element.

In practice, as the liner is inflated, because of its axial length limitation, it stretches and bulges radially inwardly. Thus, the transmural pressure of the liner is directed in the radially outward direction. Therefore, the pressure applied to the heart is less than the pressure applied to the liner. In addition, due to the bulging of the liner, the heart is deformed into an hour-glass shape. In other words, the outer central portion of the surfaces of the ventricles of the heart is deformed inwardly from its normally convex shape into a concave shape (i.e., the heart is indented). The transmural pressure of the indented portion of the heart wall is directed in the radially outward direction and, thus, is subtracted from the fluid pressure that is supplied within the liner to the outer surface of the heart. Thus, this transmural pressure is also subtracted from the fluid pressure that is applied within the liner. In other words, the heart wall itself is fighting against the externally applied force. Thus, the externally applied force in the Anstadt type device does not cooperate with the heart's own natural compressive forces during the systolic phase. It actually fights against the heart's natural motion even when the pressure is applied in synchrony with the natural systolic phase of the heart.

Consequently, the fluid pressure applied within the liner must overcome the transmural pressure created in the liner and in the heart wall. Therefore, a relatively high pressure must be applied within the liner (e.g., 150–200 mm Hg) to achieve any assistance in circulation support.

Thus, the liner of the Anstadt patents applies pressure to the heart in a non-uniform manner. Such liners are made from a silicone rubber elastomer, which, when inflated, are inherently distended and assume the shape illustrated in FIG. 9 of the '804 patent and FIG. 3 of the '298 patent. The liner of the Anstadt patents causes the heart to indent in its center portion, while, undesirably, allowing the heart ventricles to expand at their upper and lower portions. Thus, the devices according to the Anstadt patents inefficiently assist in pumping blood to and from the heart. As a result, substantial force needs to be applied to the pressure side of the liner (i.e., $P_{in}$) to cause displacement of the blood existing in the ventricle. A considerable portion of the force that is applied to the pressure side of the liner is wasted because a transmural pressure is created in the liner and the heart wall.

Another disadvantage of the prior art stems from the same feature. The increased force or pressure applied to the central portion of the ventricles' outer surface causes the heart to deform into an unnatural shape and eventually causes trauma (e.g., bruises) to the heart, especially if the prior art device is operated for a relatively extended period of time.

The ventricle portion of the heart normally has an outer convex shape during both the systolic and diastolic phases. The present inventors have surprisingly discovered that if a predetermined portion of the ventricle portion of the heart is assisted at a given externally and uniformly applied force, during the systolic phase, into its natural, albeit somewhat smaller in volume, convex shape, a great increase in the amount of fluid being pumped by the heart can be achieved compared to the same force applied according to the prior art methods. This is due, as the inventors discovered, to the fact that in the present invention the pressure applied to the heart surface and the pressure generated by contracting the heart wall add up to produce higher pressures in the ventricles without additional oxygen consumption by the ventricular wall. Therefore, by the non-distorting compression of the heart, the present invention assists the heart in generating higher blood pressure and blood flow while utilizing low and safe compression pressures.

Thus, it is an object of the present invention to provide an apparatus and method for efficiently assisting the mechanical compression of the heart, especially during the systolic phase. It is another object to provide such an apparatus and method without unduly deforming the natural shape of the heart during the mechanical compression of the heart.

It is a further object of the present invention to provide a device and method for assisting heart function, which applies substantially uniform fluid pressure against the exterior surface of at least a portion of the ventricular portion of the heart during the systolic phase.

The devices disclosed by the Anstadt patents each apply a vacuum pressure to a lower portion of the cup to prevent the heart from being ejected from the cup during the systolic compressing phase. In the '298 patent, Anstadt discloses that the vacuum communicates through opening 16 at the bottom of the liner and carries vacuum into space 6. However, in practice, only a relatively small portion of the apical portion of the heart actually plugs opening 16 and, therefore, the vacuum holding force is applied only to the portion of the heart proximate to opening 16. The application of a relatively large vacuum to such a small surface of the heart, especially in view of the large external force that needs to be applied to perform the holding function, causes further trauma to the heart. Accordingly, it is a further object of the present invention to provide an apparatus that applies a vacuum holding force over a greater relatively flat side surface area of the heart. It is still a further object of the present invention to provide a device and method that applies a vacuum holding force in such a manner so as to cause considerably less trauma to the heart.

SUMMARY OF THE INVENTION

In a preferred embodiment demonstrating features, objects and advantages of the present invention an apparatus and method for assisting a heart to pump blood by substantially uniformly compressing at least a portion of the heart ventricle during the systolic phase comprises a housing that defines an internal chamber within which the heart is placed. A fluid port is connected to the housing to supply fluid to the internal chamber of the housing. Uniform pressure is applied to a majority portion of an exterior surface of the ventricles of the heart so that the ventricles are substantially uniformly deformed.

In another preferred embodiment of the present invention an apparatus for assisting a heart to pump blood comprises a housing defining a chamber for receiving the heart. The housing has a membrane connected to the housing to divide the chamber into a first outer chamber and a second inner chamber. The housing has a bottom opening. A conduit is disposed in the opening. The conduit has a first axial end and a second axial end. The second axial end has a cup shape and is disposed in the second chamber. A flexible, perforated member is connected to the second axial end of the conduit for supporting a heart placed within the second chamber.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein:

FIG. 1 is a cross-sectional view of the apparatus according to the present invention;

FIG. 2 is a cross-sectional view of the apparatus with a heart placed therein in a diastolic phase.

FIG. 14 is a cross-sectional view taken along lines 14—14 of FIG. 12 and looking in the direction of the arrows;

FIG. 15 is a perspective view of an axially adjustable tubular conduit used in the apparatus of FIG. 12;

FIG. 16 is a cross-sectional view of the apparatus according to FIG. 12, including the conduit of FIG. 15;

DETAILED DESCRIPTION OF THE PREFERRED EMBODIMENT

Figure 4:
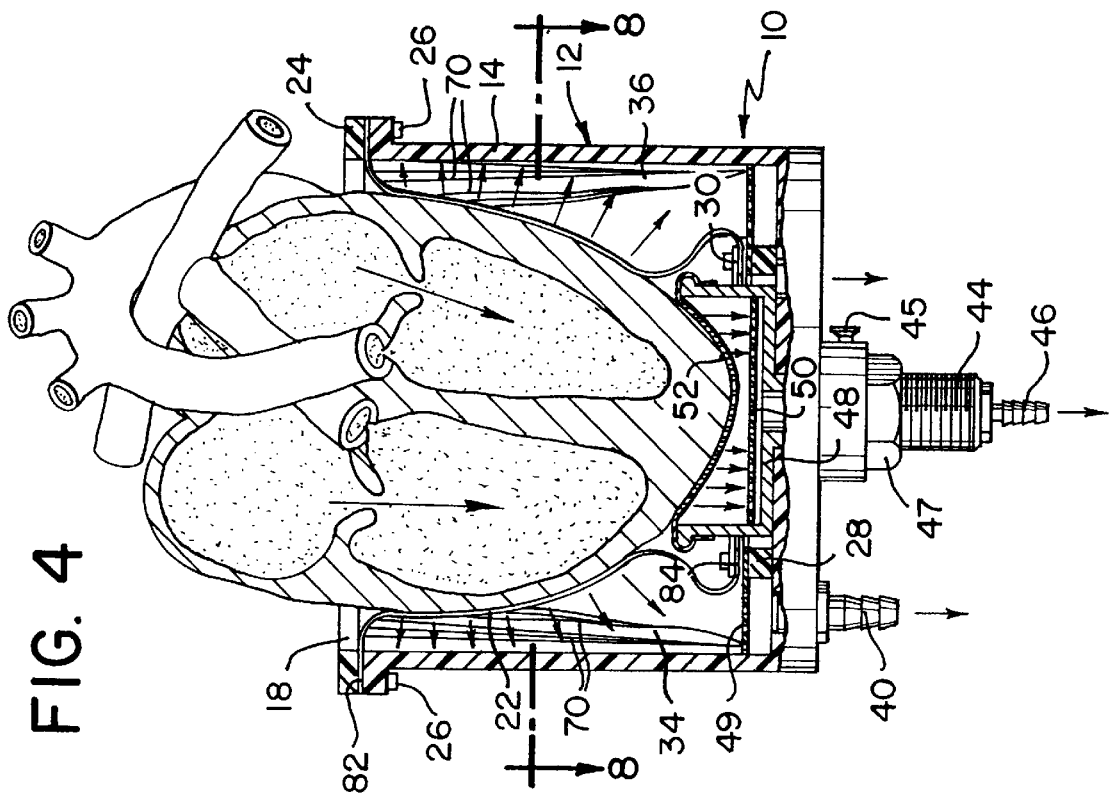
FIG. 4 is a cross-sectional view of the apparatus according to a second embodiment of the present invention with a heart placed therein in a diastolic phase.

Referring now to FIG. 1, an apparatus 10 for assisting a heart to pump blood is illustrated. Assisting is defined to mean both assisting a beating heart and resuscitating a heart that is not beating. In the illustrated embodiment, the apparatus includes a housing 12 comprised of a generally cylindrical wall 14 having at one end an axial end wall 16. Housing 12 can have other shapes than a cylinder, such as, for example, conical, cup- or cubic-shape, etc. A second axial end 18 of housing 14 is preferably open. Cylindrical wall 14 and end wall 16 define an internal chamber 20.

A fluid-impermeable flexible barrier membrane 22, of generally cylindrical shape, has its bottom end connected with a fluid-tight connection to the lower end wall 16 of the housing and its upper end connected with a fluid-tight connection to the upper end 18 of the housing. As illustrated in FIG. 1, an upper end 82 of barrier 22 is fastened to the housing by being clamped between the housing upper end 18 by an annular ring plate 24 and a plurality of fasteners 26. Fasteners 26 can be threaded or any other fluid tight fastening means can be used. The lower end 84 of barrier 22 is connected to the lower portion of housing 12 by being clamped (or otherwise securely fastened in a fluid-tight manner) between a first annular ring plate 28 and a second annular ring plate 30, which is mounted to the axial end wall 16 of housing 12 via a plurality of threaded fasteners 32.

Barrier membrane 22 divides chamber 20 into a first heart receiving chamber 34 and a second pressure fluid receiving chamber 36. A sufficient amount of barrier material in the axial direction should be provided, as illustrated in FIG. 1, to permit the material to reach the heart during the systolic phase without causing the material to be stretched. Thus, no transmural pressure is created in the barrier material. Barrier 22 is made of a fluid-impermeable material that has sufficient flexibility so that the material conforms to and applies a uniform pressure to the outer dimensions of a heart that is placed within heart receiving chamber 34. Additionally, the barrier material should be sufficiently flexible so that substantially no transmural pressure is created in the barrier. In other words, the fluid pressure on one side of the barrier is equal to the fluid pressure on the opposite side of the barrier.

In a preferred embodiment, the barrier material is a substantially inelastic film (i.e., substantially unyielding and non-stretchable) that is reinforced by a tear-resistant preferably woven material. However, if the material is sufficiently thin (for example, having a thickness of 0.5 mm or less), an elastic material such as, for example, silicone rubber or polyurethane, may be used. Preferably, barrier 22 is made of a polyethylene terephthalate ("PET") material having a thickness from 0.01–0.02 mm and more preferably about 0.013 mm (i.e., 0.5 mil). PET is a polyester sheeting material and is more commonly known by its trade name MYLAR®. Of course, other materials which are of sufficient flexibility to permit the material to completely conform to the outer dimensions of an object placed within the device and apply substantially uniform pressure to the object (i.e., having good drapeability), without creating a transmural pressure within the material may be used. Examples of such materials include, but are not limited to, polytetrafluoroethylenes ("PTFEs" such as, e.g., GORTEX®), vinyl chloride-vinylidene chloride copolymers (e.g., SARAN WRAP®), polyurethane and any other fluid-impermeable, biocompatible material that will not create a transmural pressure when inflated.

A through bore 38 disposed within end plate 16 provides fluid communication to second chamber 36. A fluid connecting inlet 40 is connected to end plate 16 and bore 38. Inlet port 40 is to be connected to a pressure fluid supply source (not shown) to alternately supply and remove pressurized fluid to chamber 36 in a manner that is well known in the art. An annular screen 49 is mounted within second chamber 36 and is fixed in place between barrier 22 and first annular plate 28. Screen 49 aids to more uniformly distribute the pressure fluid within chamber 36 that is supplied from inlet port 40.

Axial end plate 16 includes a second through bore 42 to apply a vacuum to the first, heart receiving, chamber 34 in a manner that is also well known in the art. A tubular conduit 44 is slidably received within bore 42 such that tubular conduit 44 is permitted to have limited movement in the housing axial direction. A set screw 45 and a holding nut 47 are used to selectively fix the vertical position of conduit 44 relative to end plate 16.

The U-shaped cup member 48 is illustrated in solid lines in FIG. 1 at a first lower limit position and in phantom at a second upper limit position with respect to end plate 16. A lower end of tubular conduit 44 is connected to a fluid inlet 46, which is connected to the vacuum source (not shown).

Fluid conduit 44 has an upper end 86 that is integrally connected to the bottom wall 88 of U-shaped cup member 48 that includes, in the illustrated embodiment, a first screen 50 and above it a second, perforated, heart support net 52. First screen 50 is spaced from the bottom wall 88 of cup member 48 to aid in the distribution of the vacuum within chamber 34 to a relatively large surface area of the heart apex. Heart support net 52 is preferably made of an elastic material, such as silicone rubber. Net 52 is stretched over the outer periphery of the free end of cup member 48 and normally has a planar shape, as illustrated in solid lines in FIG. 1. When a heart is placed on net 52, it deforms into a concave shape (as viewed from above and as illustrated in dashed lines) and acts as a "hammock" to receive and support the lower portion of the heart when it is placed in chamber 34. Less trauma is caused to the heart because support net 52 is formed from a relatively soft material and because the vacuum holding force is applied over a greater surface area.

Axial end wall 16 includes a third throughhole 60. Throughhole 60 preferably includes a one-way valve 62 that permits fluid only to be removed from the heart receiving chamber 34. After the first few initial diastolic/systolic cycles, the amount of fluid remaining in chamber 34 will be minimal (See FIGS. 2 and 3).

The operation of the apparatus according to the present invention will now be described with reference to FIGS. 2 and 3. Conduit 44 is first moved to any axial position between its upper limit position and its lower limit position. Conduit 44 is illustrated in lower limit position. However, it is to be understood that the surgeon will typically choose the position of conduit 44 (and thus the position of heart support net 52) based on the size of the heart that is being placed within chamber 34. This eliminates the need for cups of many sizes. The only constraint is the size of the chest cavity.

A heart is placed within chamber 34 of housing 12 so that the heart lower portion is supported by perforated net 52. A vacuum source is connected to port 46 to assist in holding the heart within chamber 34. A pulsating fluid pressure is transmitted through port 40 to cyclically pressurize and depressurize chamber 36. The maximum fluid pressure is preferably 50–100 mm Hg above atmospheric pressure, and the minimum fluid pressure is preferably –50 to –100 mm Hg below atmospheric pressure. However, for resuscitation (i.e., the heart is not beating), the maximum fluid pressure is preferably about 150 mm Hg. The liners of the Anstadt patents are probably inflated to about 150 mm Hg above atmospheric pressure for both assistance and resuscitation because these types of liners overpower the heart.

Figure 3:
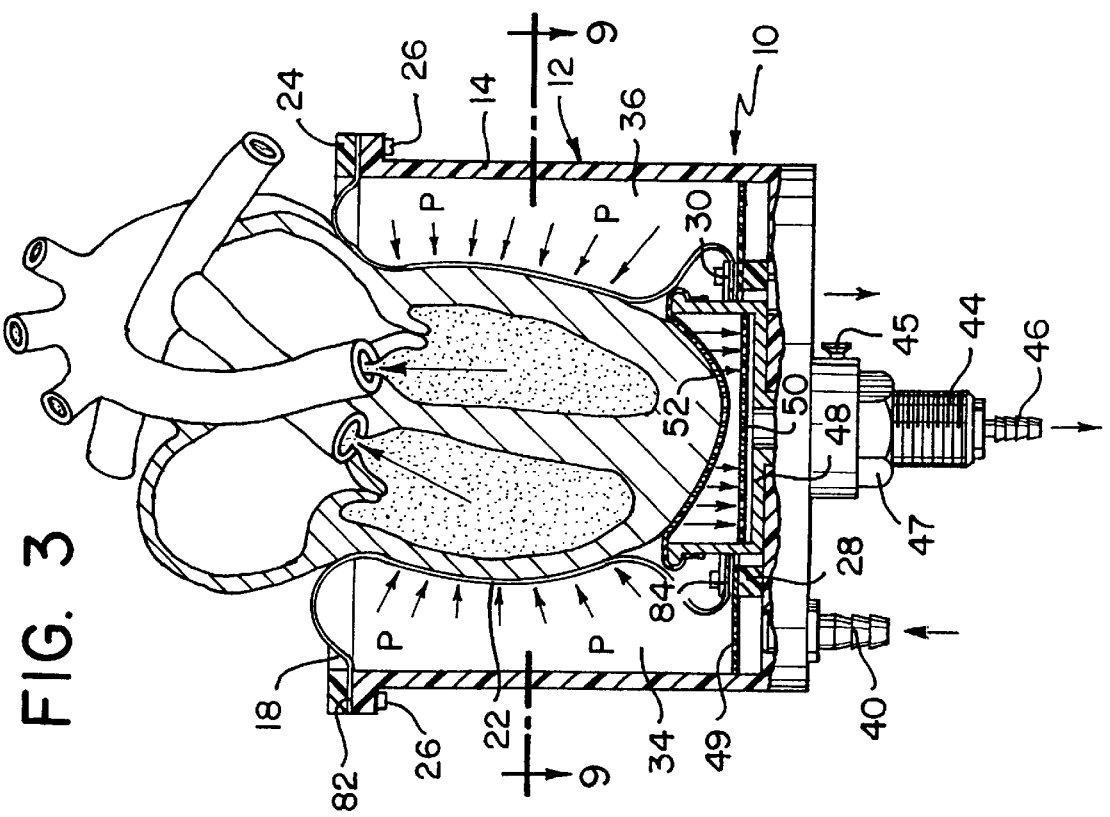
FIG. 3 is a cross-sectional view of the apparatus with a heart placed therein in a systolic phase.
Figure 8:
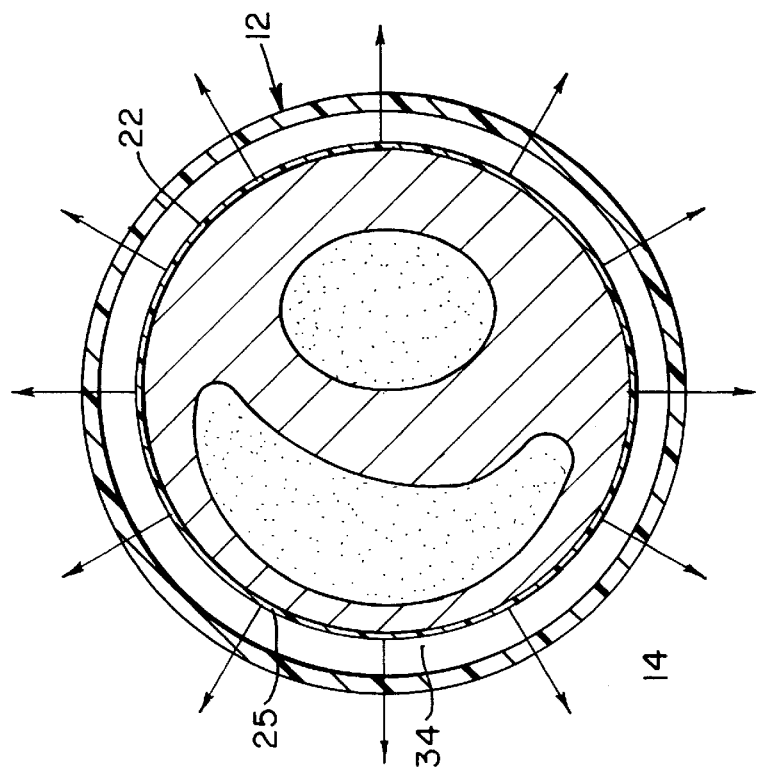
FIG. 8 is a cross-sectional view taken along lines 8—8 of FIGS. 2 and 4 and looking in the direction of the arrows.
Figure 9:
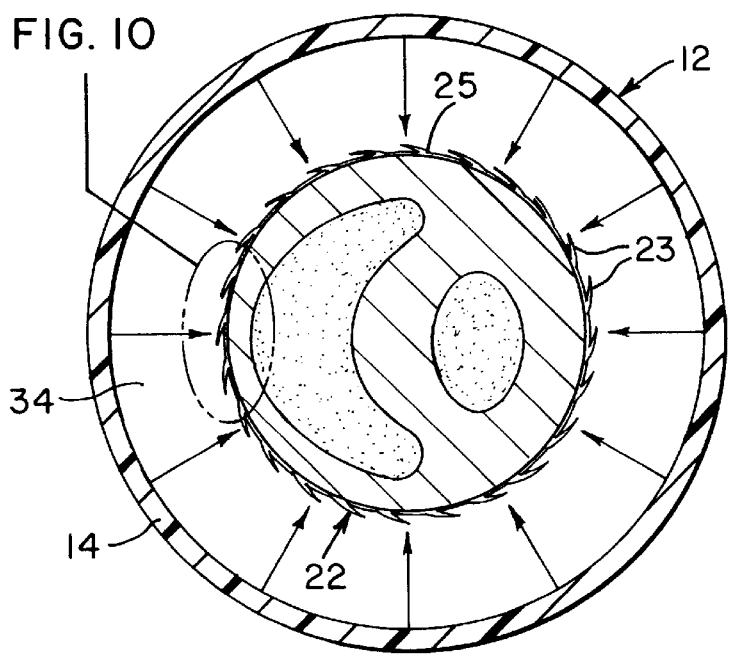
FIG. 9 is a cross-sectional view taken along lines 9—9 of FIGS. 3 and 5 and looking in the direction of the arrows.
Figure 10:
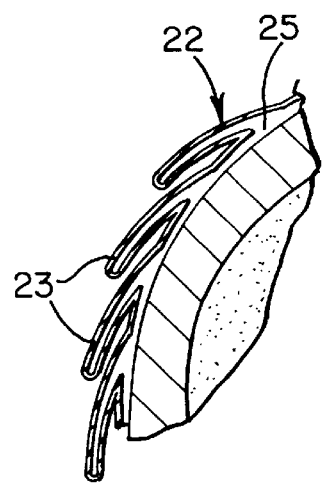
FIG. 10 is an enlarged view of detail A of FIG. 9.
Figure 11:
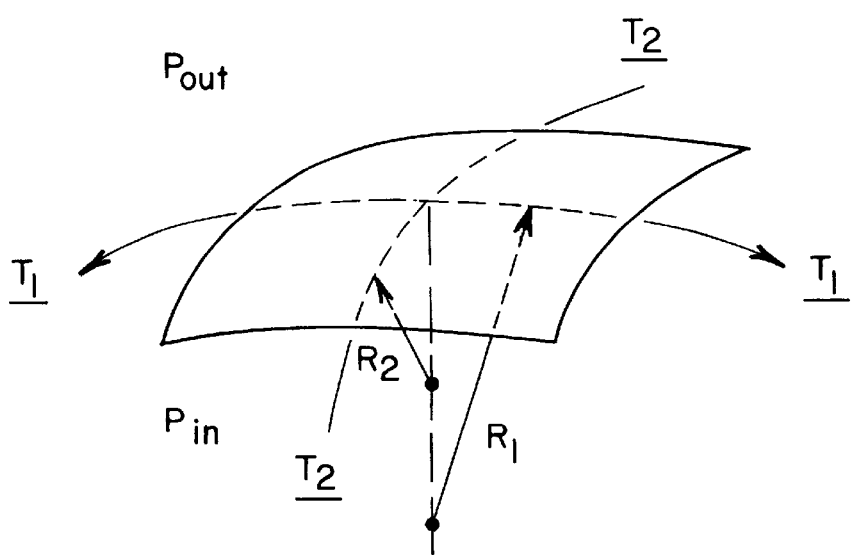
FIG. 11 is a schematic illustration of a curved differential surface element of a stretched liner wall.

As fluid pressure increases within chamber 36, barrier 22 first conforms to the exact shape of the heart and thereafter applies a uniform pressure P to the entire external surface of the heart that is in contact with barrier 22, as illustrated in FIGS. 3, 9 and 10. As pressure within chamber 36 is increased, barrier 22 conforms to the outer surface 25 of the ventricles of the heart. Thus, barrier 22, because it is made of sufficiently flexible material, creates a plurality of folds 23 about the outer surface 25 of the ventricular portion of the heart. For illustrative purposes only, the outer surface 25 of the ventricular portion of the heart is not illustrated in FIGS. 8 and 9 because it is substantially coextensive with barrier 22.

As discussed above, barrier 22 is made of a material which does not create a transmural pressure even when pressure is applied in chamber 36. In other words, the pressure applied to the exterior ventricular surface 25 of the heart is essentially the same as the pressure within chamber 36. Thus, as pressure within chamber 36 increases to the predetermined maximum pressure, the heart is compressed substantially uniformly such that the normally convex outer shape of the heart is maintained during the pressurized (i.e., systolic) cycle (FIG. 3). Thus, the transmural pressure of the heart wall is directed in the radial inward direction and, thus, is added to the fluid pressure applied within chamber 36. Therefore, the present invention helps the heart to generate pressure within the ventricles.

Because no transmural pressure is created in barrier 22 and the transmural pressure in the heart wall is additive, substantially lower fluid pressures can be utilized to obtain even better hemodynamics than compared to prior art systems. Using substantially lower driving fluid pressures considerably decreases the risk of causing trauma to the heart. Additionally, because lower driving pressures are utilized, a pneumatic or hydraulic driving system can be used, which has a relatively small size and complexity due to the reduced gas or liquid pressure requirements.

Of course, fluid pressure is not applied against the portion of the heart disposed against member 52 nor against any atrial portion of the heart (disposed above ring plate 24).

The timing of applying the pulsating fluid pressure is preferably synchronized with the natural timing of the heart's systolic and diastolic phases.

Once the systolic phase is complete, the fluid pressure transmitted through port 40 is reduced in a controlled manner to initiate the diastolic phase, as is well known in the art. When the predetermined minimum pressure is reached within chamber 36, at which time no pressure is applied to the exterior of the ventricular walls of the heart, barrier 22 may still conform to the exterior shape of the heart, or if the negative pressure is low enough, barrier 22 may withdraw to the interior walls of cylindrical wall 14. It is to be noted that screen 49 prevents barrier 22 from blocking the flow of fluid from chamber 36 during the diastolic phase. Thereafter, the systolic and diastolic phases continue in alternating fashion for as long as needed. Once the device is no longer needed to aid in assisting the heart to pump blood, the connection of the pulsating fluid pressure source to port 40 can also be disconnected and the connection of the vacuum source to port 46 can also be disconnected. The heart can then be removed from chamber 34, and the device can be removed from the patient's chest cavity.

Figure 5:
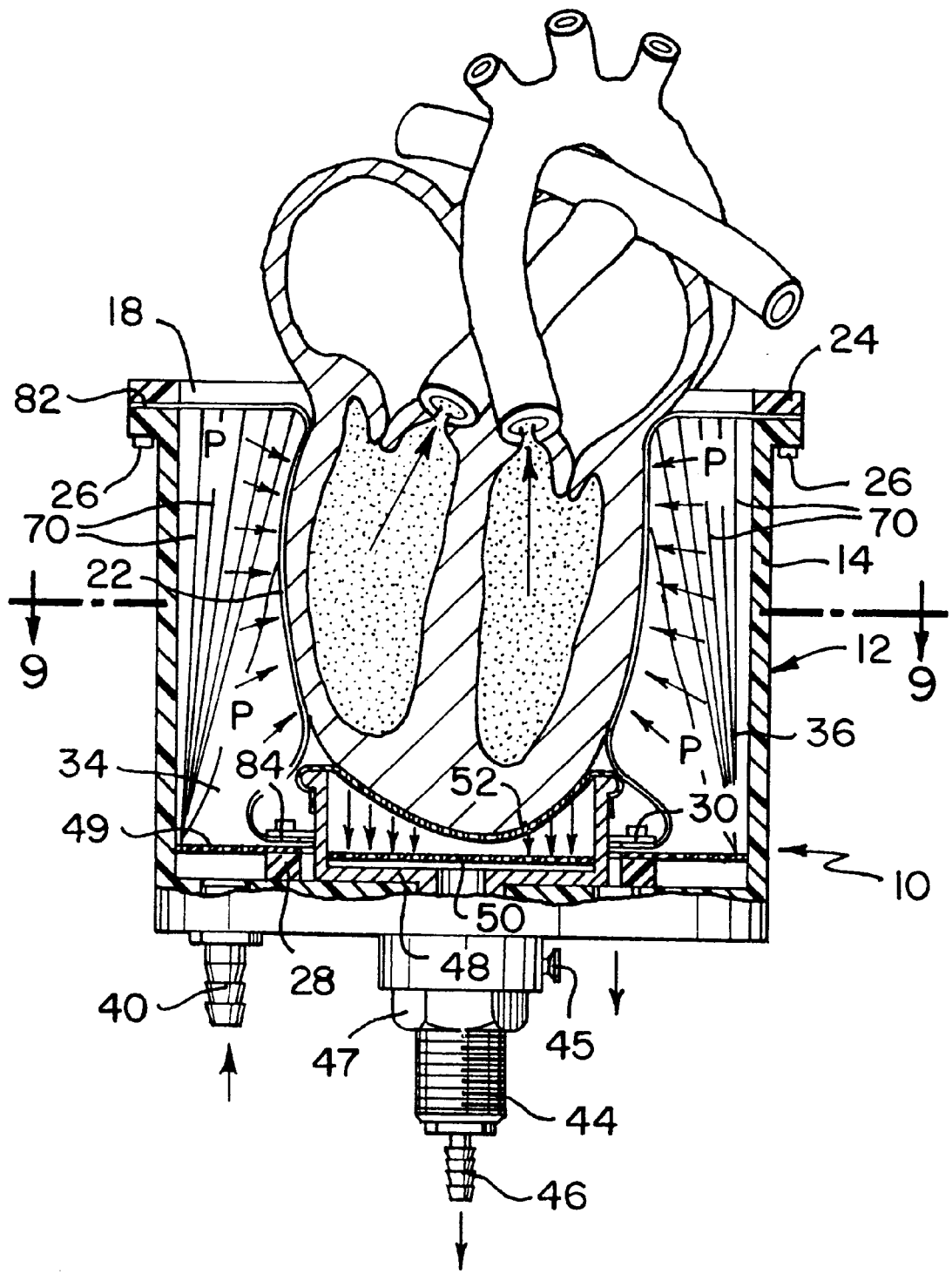
FIG. 5 is a cross-sectional view of the apparatus according to a second embodiment of the present invention with a heart placed therein in a systolic phase.

Referring now to FIGS. 4 and 5, a second embodiment of the invention is illustrated. This embodiment is similar to the embodiment illustrated in FIGS. 1–3, and therefore, like reference numerals will be used to designate like elements. This embodiment differs from the embodiment illustrated in FIGS. 1–3 in that a plurality of cords 70 are utilized to limit the amount of movement of barrier 22. Bottom ends of the cords 70 are fixed to the lower end of housing 12 adjacent to screen 49. Of course, the bottom ends of the cords could be fixed to any portion of cylindrical wall, including adjacent to the upper end 18, but this is not preferred. The opposite end of the cords 70 are fixed to barrier 22 adjacent to the upper axial end 18 of housing 14. Cords 70 are preferably made from an inelastic material and therefore limit the amount of upward movement of barrier 22 away from the axial lower end wall 16 of housing 12. Of course, cords 70 could also be made of an elastic material, but this is not preferred. Without the use of cords 70, when chamber 36 is pressurized, barrier 22 would be free to extend beyond the second axial end 18 and, therefore, outside of housing 12. Cords 70 limit the upward movement of barrier 22 and therefore prevent barrier 22 from being disposed outside of housing 12 during the systolic phase (See FIG. 5). It is preferable to limit the upward movement of barrier 22 so that during the diastolic phase, barrier 22 will not be caught outside of the housing. Additionally, if cords 70 are not used, barrier 22 will likely move from inside of the housing to outside of the housing. This movement of the upper portion of the barrier in and out of the housing will cause wear on the housing and barrier, which may eventually cause a rupture of the barrier. Further, if barrier 22 is disposed outside of the housing during the systolic phase, the atrium may be inadvertently compressed by the barrier.

Figure 6:
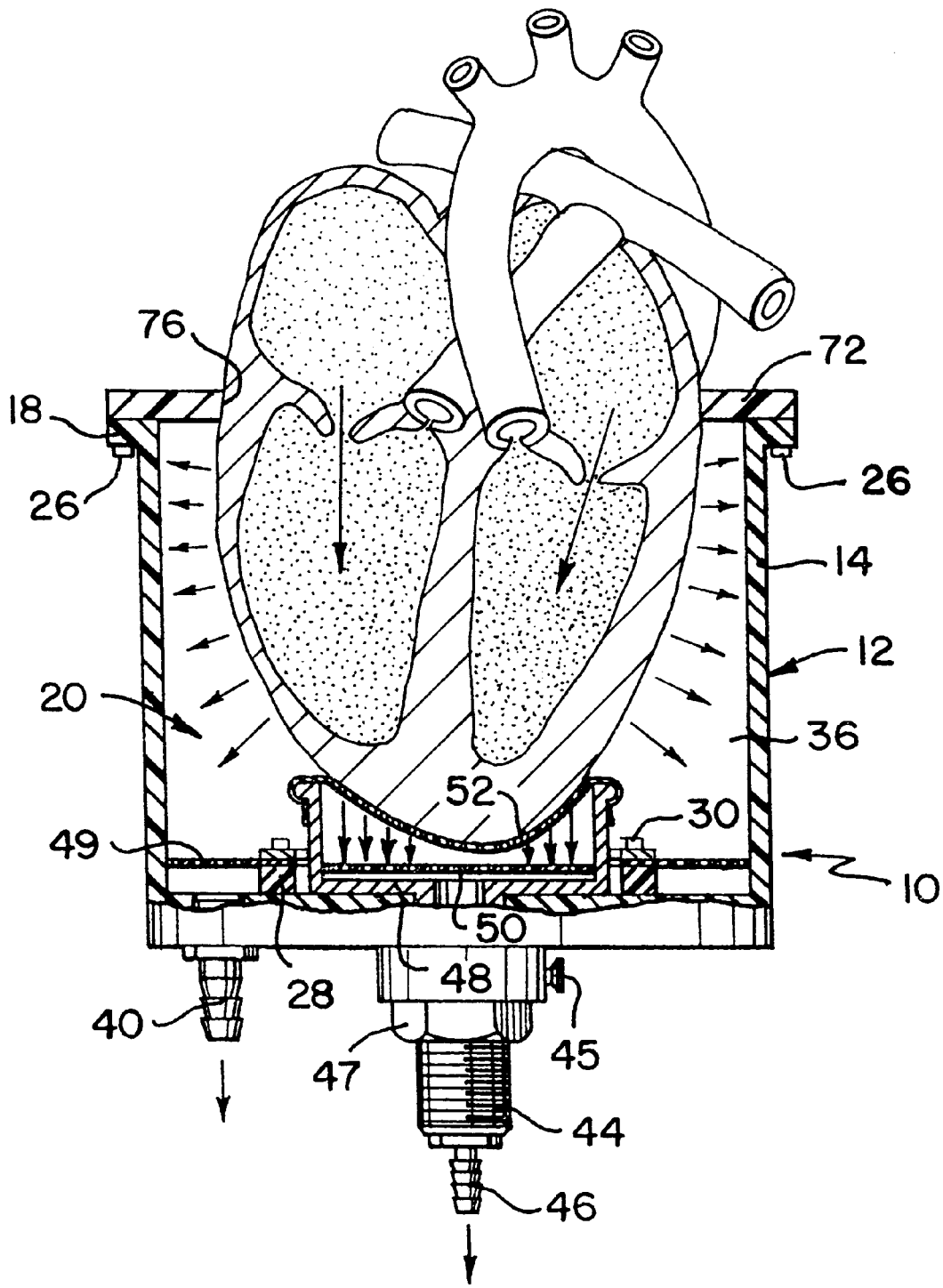
FIG. 6 is a cross-sectional view of the apparatus according to a third embodiment of the present invention with a heart placed therein in a diastolic phase.
Figure 7:
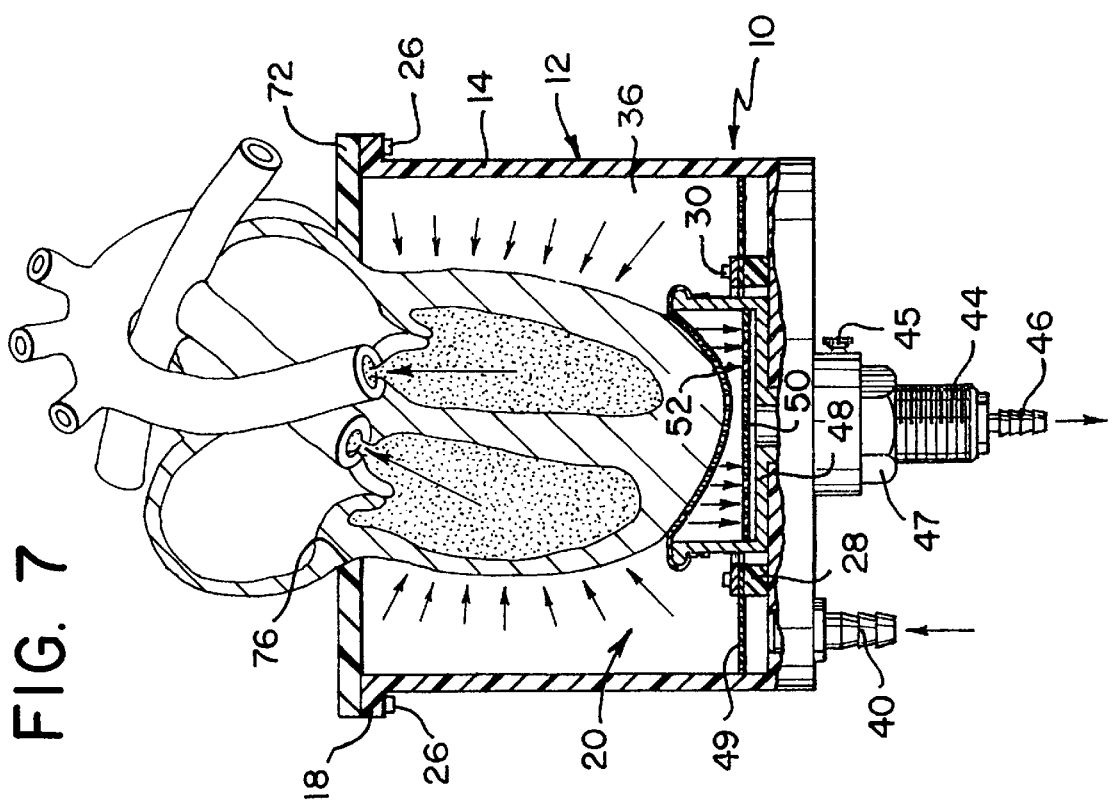
FIG. 7 is a cross-sectional view of the apparatus according to a third embodiment of the present invention with a heart placed therein in a systolic phase.

Referring now to FIGS. 6 and 7, a third embodiment of the invention is illustrated. This embodiment is substantially similar to the embodiments illustrated in FIGS. 1–3 and, therefore, like reference numerals are used to designate like elements. This embodiment differs from the embodiment illustrated in FIGS. 1-3 in that an iris 72 is used to form a seal between the open axial end 18 of housing 12 and a heart that is placed within the internal chamber 20 of the housing. Iris 72 is preferably made from a polycarbonate resin, such as, for example, LEXAN®. Iris 72 is fixed to the second upper open axial end 18 of the housing via a plurality of fasteners 74. Iris 72 acts as a diaphragm that is automatically expands and contracts its opening size to effect an adequate fluid seal 76 with respect to the heart. Thus, in accordance with this third embodiment, barrier 22 and one way valve 62 are omitted.

In operation, pressurized fluid is alternately supplied and removed to and from chamber 20 through port 40 to cyclically pressurize and depressurize chamber 20. As fluid pressure increases within chamber 20, a uniform pressure P is applied to substantially the entire external surface of the heart that is disposed within chamber 20. The heart is directly compressed substantially uniformly over its entire surface by the applied pressures such that the normal convex outer shape of the heart is maintained during the pressurized (i.e., systolic) cycle (See FIG. 7). It is to be noted that as viewed from the heart's perspective, the embodiments of FIGS. 1–5 are identical to the embodiment of FIGS. 6 and 7, because barrier 22 essentially has no transmural pressure created therein.

The device of the present invention can be made in various sizes depending on the size of the person or animal for whom it is to be used on. The device's outer dimensions are sized to fit within the chest cavity of the patient. Typically, for humans, only two or three adult sizes may be required along with one or two pediatric sizes.

The pressure fluid supplied and removed from port 40 is preferably a pneumatic fluid, such as, for example, air, carbon dioxide or an inert gas (e.g., Argon). Alternatively, the pressure fluid may be a hydraulic fluid, such as, for example, water or saline. When no barrier is used (FIGS. 6 and 7), the pressure fluid is preferably air with vapors of normal saline or wet carbon dioxide so that the exterior surface of the heart will not dry out.

Referring now to FIGS. 12–17, and in accordance with a fourth embodiment of the present invention, an apparatus 110 for assisting a heart to pump blood is illustrated. Assisting is defined to mean both assisting a beating heart and resuscitating a heart that is not beating. In the illustrated embodiment, the apparatus includes a housing 112 comprised of a generally partial or D-shaped (in cross-section) cylindrical wall 114 and a substantially flat manifold pad 122. It is envisioned that the housing 112 can have other shapes than a cylinder, such as, for example, conical-, cupor cubic-shape, etc. Connected to one end of the housing is an axial end wall 116. A second axial end 118 of the housing 112 is preferably open for convenient capturing of the heart. The cylindrical wall 114 and the axial end wall 116 define an internal chamber 120. The manifold pad 122 is formed with a crescent-shaped radial cross-section and is fixedly connected to the cylinder wall 114. The manifold 122 has an upper heart supporting surface 123 and includes a plurality of spaced-apart and downwardly depending bores 126 disposed in fluid communication with a common bore 128. Bore 128 can be fluidly connected to a vacuum source via port 131 to preferably apply constant suction pressure. The pad or heart support platform 122 is preferably made of an elastic material, such as silicone rubber.

Figure 12:
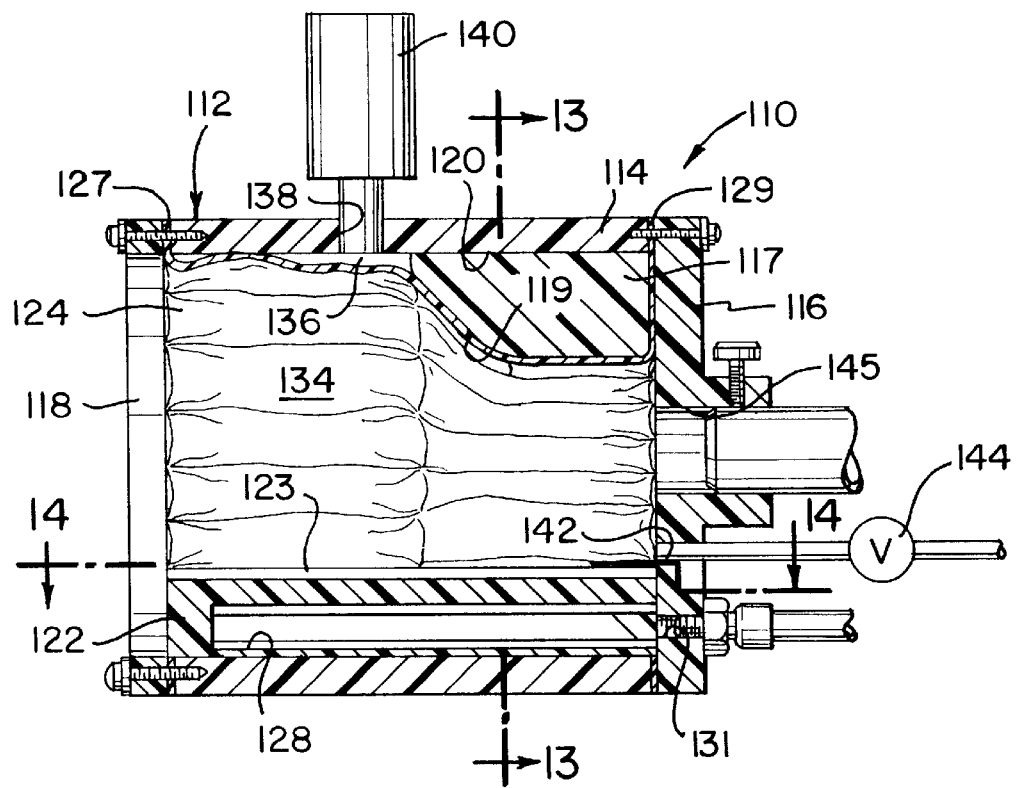
FIG. 12 is a cross-sectional view of the apparatus according to a fourth embodiment of the present invention.
Figure 13:
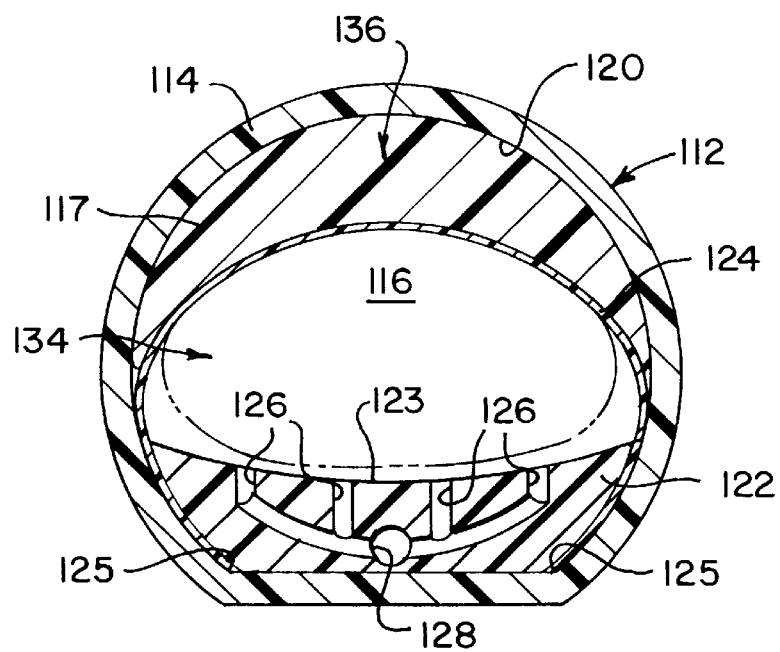
FIG. 13 is a cross-sectional view taken along lines 13—13 of FIG. 12 and looking in the direction of the arrows.
Figure 17:
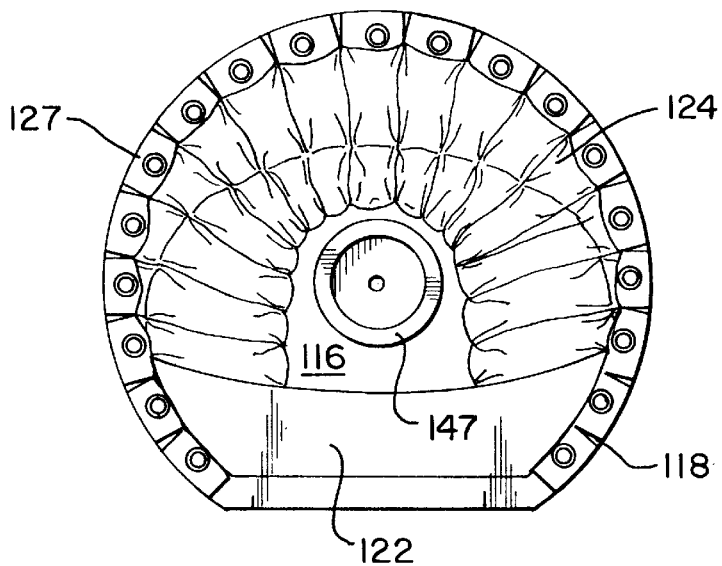
FIG. 17 is a left-side view of the apparatus of FIG. 16.

A fluid-impermeable flexible barrier membrane 124, of a generally inverted U-shape in cross-section, has its two bottom ends 125 connected with a fluid-tight connection to the juncture of cylinder wall 114 and pad 122. The sides 127, 129 of barrier 124 are mounted between cylindrical wall 114 and flange 115, and between cylindrical wall 114, insert 117 and axial end wall 116, respectively. Insert 117 is mounted in chamber 120 at the juncture of cylindrical wall 114 and axial end wall 116. Insert 117 has a smooth internal curved surface 119 that is shaped to receive the apex portion of the heart. Barrier membrane 124 divides chamber 120 into a first heart receiving chamber 134 and a second pressure fluid receiving chamber 136. A sufficient amount of barrier material in the axial direction should be provided, as illustrated in FIGS. 12, 13 and 17, to permit the material to reach the heart during the systolic phase without causing the material to be stretched. Thus, no transmural pressure is created in the barrier material. Barrier 124 is made of a fluid-impermeable material that has sufficient flexibility so that the material conforms to and applies a uniform pressure to the outer dimensions of a heart that is placed within heart receiving chamber 134. Additionally, the barrier material should be sufficiently flexible so that substantially no transmural pressure is created in the barrier. In other words, the fluid pressure on one side of the barrier is equal to the fluid pressure on the opposite side of the barrier.

In a preferred embodiment, the barrier material is a substantially inelastic film (i.e., substantially unyielding and non-stretchable) that is reinforced by a tear-resistant, preferably woven material. However, if the material is sufficiently thin (for example, having a thickness of 0.5 mm or less), an elastic material such as, for example, silicone rubber or polyurethane, may be used. Preferably, barrier 124 is made of a polyethylene terephthalate ("PET") material having a thickness from 0.01–0.02 mm and more preferably about 0.013 mm (i.e., 0.5 mil). PET is a polyester sheeting material and is more commonly known by its trade name MYLAR®. Of course, other materials which are of sufficient flexibility to permit the material to completely conform to the outer surface of an object placed within the device and apply substantially uniform pressure to the object (i.e., having good drapeability), without creating a transmural pressure within the material may be used. Examples of such materials include, but are not limited to, polytetrafluoroethylenes ("PTFEs" such as, e.g., GORTEX®), vinyl chloride-vinylidene chloride copolymers (e.g., SARAN WRAP®), polyurethane and any other fluid-impermeable, biocompatible material that will not create a transmural pressure when inflated.

A through bore 138 disposed within cylinder wall 114 provides fluid communication to the second chamber 136. A fluid connecting inlet 140 is connected to the cylinder wall 114 and the bore 138. The inlet port 140 is to be connected to a pressure fluid supply source (not shown) to alternately supply and remove pressurized fluid to chamber 136 in a manner that is well known in the art.

The axial end wall 116 is formed with a second through hole 142 preferably having a one-way valve 144 that permits fluid to only be removed from the heart receiving chamber 134. After the first few initial diastolic/systolic cycles, the amount of fluid remaining in the chamber 134 will be minimal (See FIG. 13). If desired, a third through hole 145 in end wall 116 has a tubular conduit 143 slidably received in through hole 145 such that tubular conduit 143 is permitted to have limited movement in the axial direction. A set screw 146 and a holding nut (not shown) are used to selectively fix the axial position of conduit 143 relative to end plate 116. Conduit 143 is in fluid communication with the vacuum source so that the heart can be further secured in position by providing a suction holding force to the apex region of the heart through the open free end 147 of conduit 143.

The operation of the apparatus according to the present invention will now be described with reference to FIGS. 12 and 13.

A heart is placed within the chamber 134 of the housing 112 so that the relatively flat surface of the heart, known as the posterior, inferior surface, is supported by surface 123 of the heart support platform 122. Housing 112 is preferably placed between the pericardium and the heart. A vacuum source is fluidly connected to bore 128 to assist in holding the heart within the chamber 134. A pulsating fluid pressure is transmitted through port 140 to cyclically inflate and deflate chamber 136. An appropriate inflation/deflation drive system for carrying out this task is disclosed in U.S. Provisional patent application Ser. No. 60/044,460, entitled Drive System For Controlling Cardiac Compression filed on Apr. 4, 1997 and assigned to the assignee of the present invention, and which disclosure is hereby fully incorporated by reference. The maximum fluid pressure is preferably 50–100 mm Hg above atmospheric pressure, and the minimum fluid pressure is preferably −50 to −100 mm Hg below atmospheric pressure. However, for resuscitation (i.e., the heart is not beating), the maximum fluid pressure is preferably about 150 mm Hg.

As fluid pressure increases within chamber 136, barrier 124 first conforms to the exact shape of the portion of the heart not resting on the platform 122 and, thereafter, applies a uniform pressure P to the entire external surface of the ventricles of the heart that is not in contact with the barrier 124, as illustrated in FIG. 13. As pressure within chamber 136 is increased, the barrier 124 conforms to the outer surface 185 of the heart. Because the barrier is made of sufficiently flexible material, a plurality of folds are created about the outer surface of the ventricular portion of the heart.

As discussed above, barrier 124 is made of a material which does not create a transmural pressure even when pressure is applied in the chamber 136. In other words, the pressure applied to the exterior ventricular surface of the heart is essentially the same as the pressure within the chamber 136. Thus, as pressure within chamber 136 increases to the predetermined maximum pressure, the heart is compressed substantially uniformly such that the normally convex outer shape of the heart is maintained during the pressurized (i.e., systolic) cycle. Thus, the transmural pressure of the heart wall is directed in the radial inward direction and, thus, is added to the fluid pressure applied within the chamber 136. Therefore, the present invention helps the heart to generate pressure within the ventricles.

Because no transmural pressure is created in barrier 124 and the transmural pressure in the heart wall is additive, substantially lower fluid pressures can be utilized to obtain even better hemodynamics than compared to prior art systems. Using substantially lower driving fluid pressures considerably decreases the risk of causing trauma to the heart. Additionally, because lower driving pressures are utilized, a pneumatic or hydraulic driving system can be used, which has a relatively small size and complexity due to the reduced gas or liquid pressure requirements.

Of course, fluid pressure is not applied against the atrial portion of the heart because the atrial portion of the heart is disposed outside of the internal chamber 120. Additionally, barrier 124 does not directly apply fluid pressure against any portion of the heart that is supported by the platform 122 or contacts tubular conduit 143. Of course, during the compressive phase, the barrier 124 applies fluid pressure to the portion of the heart not resting on the platform 122. Because the platform 122 supports the heart, an equal and opposite reactive force is applied against the portion of the heart lying on the platform 122.

The timing for applying the pulsating fluid pressure is preferably synchronized with the natural timing of the heart's systolic and diastolic phases.

Once the systolic phase is complete, the fluid pressure transmitted through the port 140 is reduced in a controlled manner to initiate the diastolic phase, as is well known in the art. When the predetermined minimum pressure is reached within the chamber 136, at which time no pressure is applied to the exterior of the ventricular walls of the heart, the barrier 124 may still conform to the exterior shape of the heart, or if the minimum pressure is negative, the barrier 124 may withdraw to the interior walls of the cylindrical wall 114. It is to be noted that a screen (not shown) may be used to prevent barrier 124 from blocking the flow of fluid from the chamber 136 during the diastolic phase. The use of a screen is fully illustrated and described above. Thereafter, the systolic and diastolic phases continue in alternating fashion for as long as needed. Once the device is no longer needed to aid in assisting the heart to pump blood, the connection of the pulsating fluid pressure source to the port 140 can be disconnected and the connection of the vacuum source to holes 131, 145 can also be disconnected. The heart can then be removed from the chamber 134, and the device can be removed from the patient's chest cavity.

The pressure fluid supplied and removed from port 140 is preferably a pneumatic fluid, such as, for example, air, carbon dioxide or an inert gas (e.g., Argon). Alternatively, the pressure fluid may be a hydraulic fluid, such as, for example, water or saline. If no barrier is used, the pressure fluid is preferably air with vapors of normal saline or wet carbon dioxide so that the exterior surface of the heart will not dry out.

Figure 18:
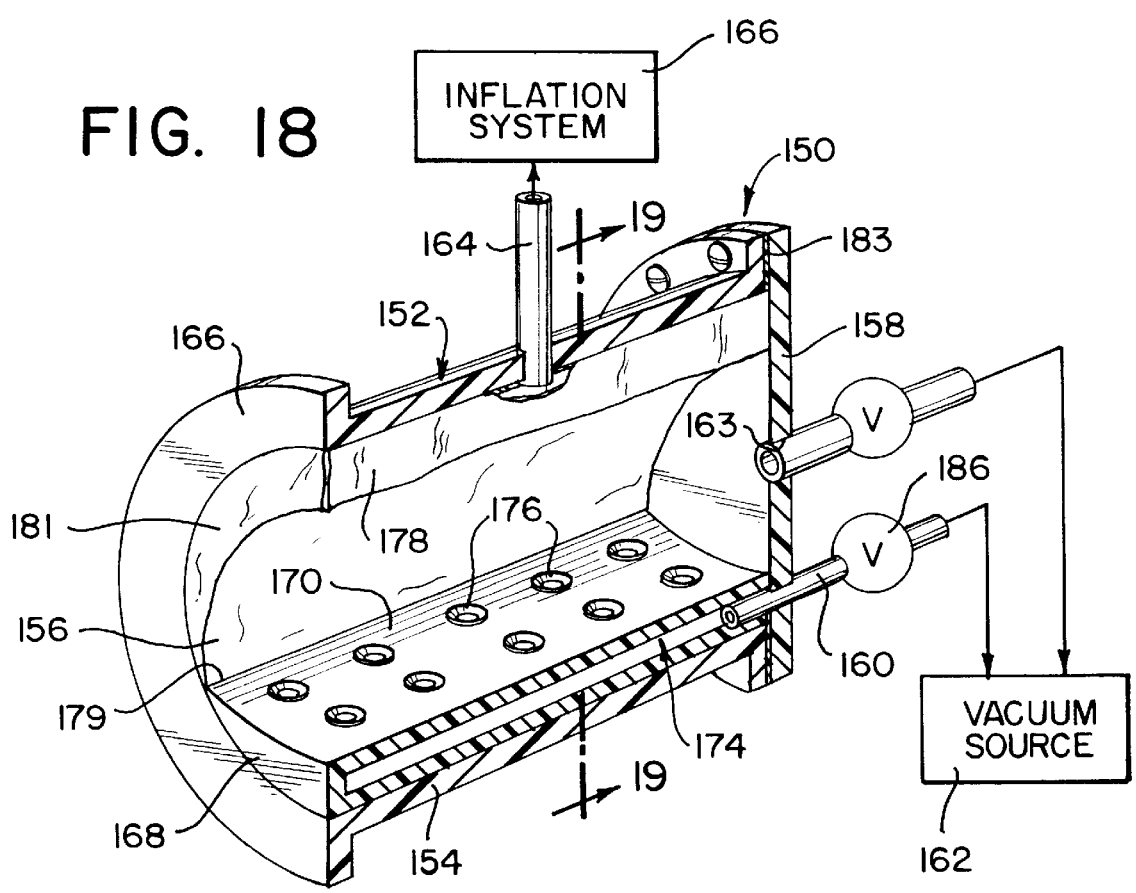
FIG. 18 is a perspective view of the apparatus according to a fifth embodiment of the present invention.
Figure 19:
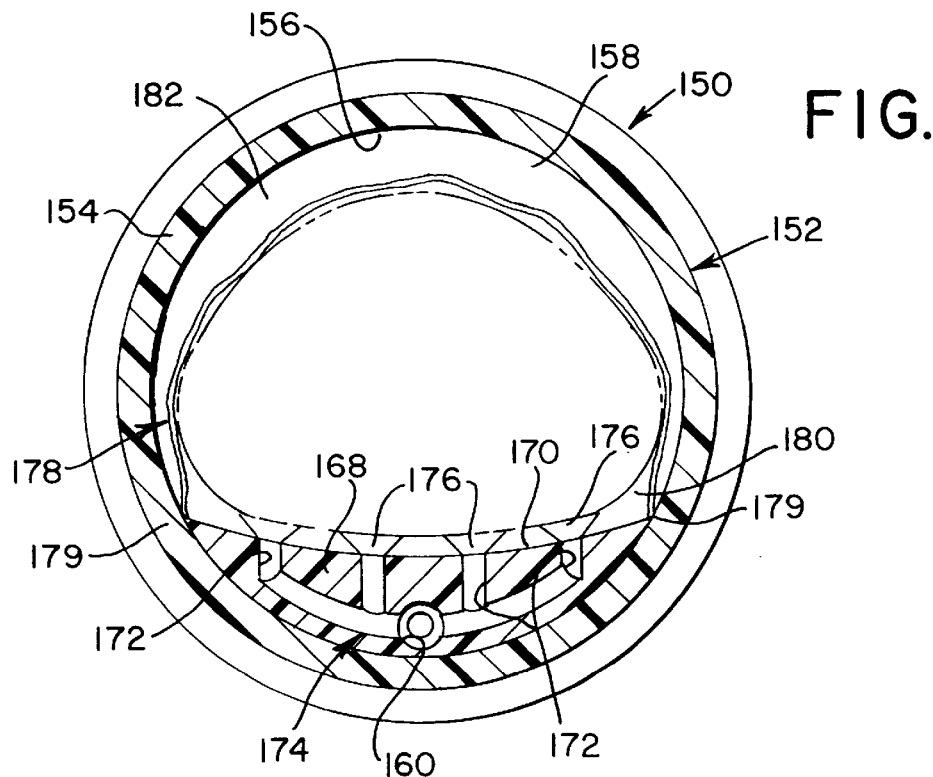
FIG. 19 is a cross-sectional view taken along lines 19—19 of FIG. 18 and looking in the direction of the arrows.

Referring now to FIGS. 18 and 19, the apparatus according to a third embodiment of the present invention, generally designated 150, includes an open ended housing 152. The housing includes a substantially circular in lateral cross-section wall 154 (FIG. 19) to define an internal cavity 156 and is complementary formed to nest within the chest cavity to minimize the movement of the heart typically associated with the insertion and retraction of the apparatus. Disposed at one end of the housing is an axial end wall 158 formed with an outlet port 160 for connecting to a vacuum source 162. As in the first embodiment, an axially adjustable tubular conduit (not shown) may be slidably received in bore 163. Bore 163 is also fluidly connected to vacuum source 162 to provide a second location to secure the heart in position. Here the open end of the tubular conduit provides a uniform suction holding force to the apex region of the heart.

An inlet port 164 is formed near the apex of the wall 154 to provide a convenient interface to an inflation system 166. A manifold pad 168 or heart support platform having a slightly concave support surface 170 closely conforms to the overall shape of the heart. The platform is formed with a plurality of upwardly opening bores 172 networked and coupled together in fluid communication to define a vacuum manifold 174. A plurality of upwardly projecting suction cups 176 (FIG. 19) mount within the bores for adhering to the posterior, inferior surface of the heart.

Mounted along the longitudinal periphery of the heart support platform 168 is a fluid-impermeable flexible barrier membrane 178 substantially similar to that disclosed in the first embodiment. The membrane comprises a generally inverted U-shape in cross-section configuration and has two bottom ends 179 sealably connected to the juncture of the housing wall 154 and the platform 168. Side 181 of barrier 178 is connected to an axial free end 166 of wall 154. The opposite side 183 of the barrier 178 is mounted between wall 154 and axial end wall 158. An insert (not shown, but similar to insert 117 of FIGS. 12–17) may be mounted in cavity 156 at the juncture of wall 154 and axial end wall 158. Membrane 178 divides the internal cavity 156 into a first heart receiving chamber 180 and a second pressure fluid receiving chamber 182. While the membrane may be constructed according to the first embodiment of the apparatus of the present invention, the inventors have discovered that by attaching a thin sheet of nylon to the membrane as a second layer of material, any possibilities of tearing are substantially minimized. In such a configuration where a layer of approximately 0.5 mil MYLAR® material is envisioned, a nylon layer of approximately 0.1 to 0.2 mm is sufficient to provide the added durability.

The vacuum source 162 couples to the vacuum manifold 174 and the outlet port 160 through a check valve 186. Sufficient vacuum is required to maintain a uniform suction across the heart platform and through the outlet port to secure the heart in a fixed position to effect efficient and reliable assistance to the heart. Of course, suction cups 176 and the optional tubular conduit also aid in holding the heart in place on the heart platform.

Operation of the apparatus according to the fifth embodiment of the present invention proceeds substantially similar to that of the fourth embodiment. Once the apparatus 150 is positioned around the heart, with the heart supported by the platform 168, the vacuum source 162 is energized to create vacuum through the manifold and secure the heart thereto. Additionally, because of the positioning of the outlet port 163, the vacuum therefrom attracts and secures the apical end of the heart to the axial wall 158, providing additional support to maintain the heart in position during operation.

Following successful positioning of the heart within apparatus 150, the inflation system 166 is activated to cyclically pressurize the fluid receiving chamber 182. As pressure within the fluid chamber increases, corresponding to the heart's systolic cycle, the membrane uniformly conforms around the heart and applies a corresponding pressure P to the entire external surface of the heart contacting the membrane. Continued pressurization causes the membrane to fold upon itself while further uniformly compressing the heart.

Like the operation of the apparatus according to the first embodiment of the present invention, membrane 178 is constructed of a material or combination of materials that does not create a transmural pressure in response to pressure within the fluid chamber 182. As a result, the pressure applied to the exterior ventricular surface 185 of the heart is essentially the same as the pressure within the chamber.

Figure 20:
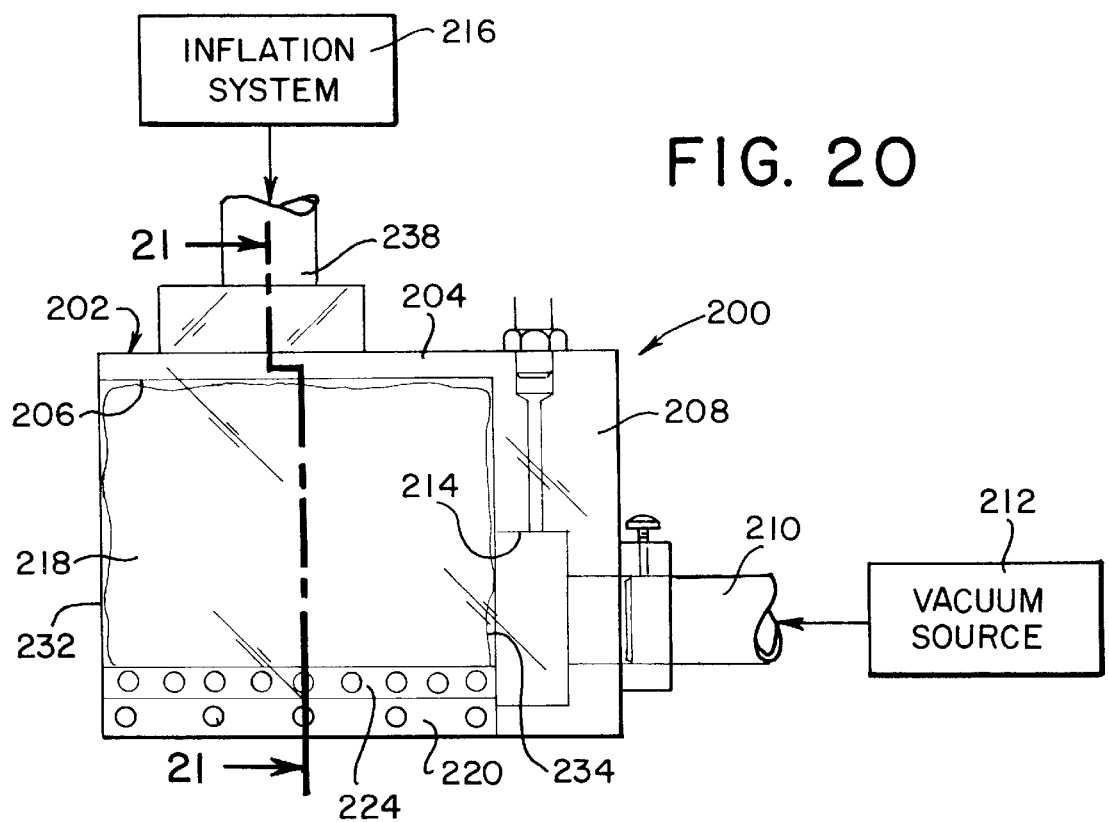
FIG. 20 is a cross-sectional view of the apparatus according to a sixth embodiment of the present invention.
Figure 21:
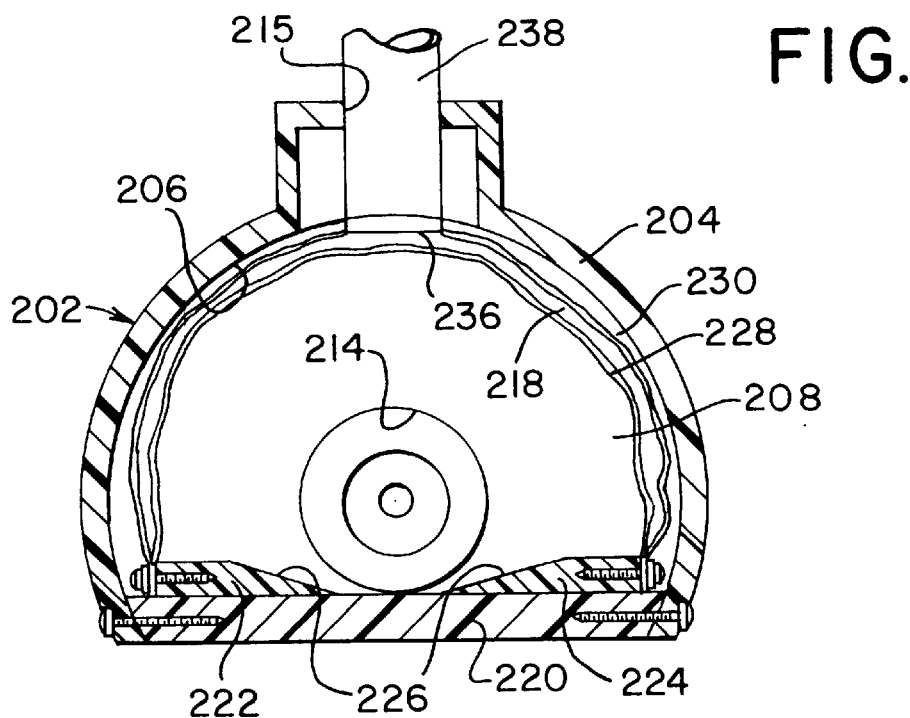
FIG. 21 is a cross-sectional view, showing a diastolic phase, taken along lines 21—21 of FIG. 20 and looking in the direction of the arrows.
Figure 22:
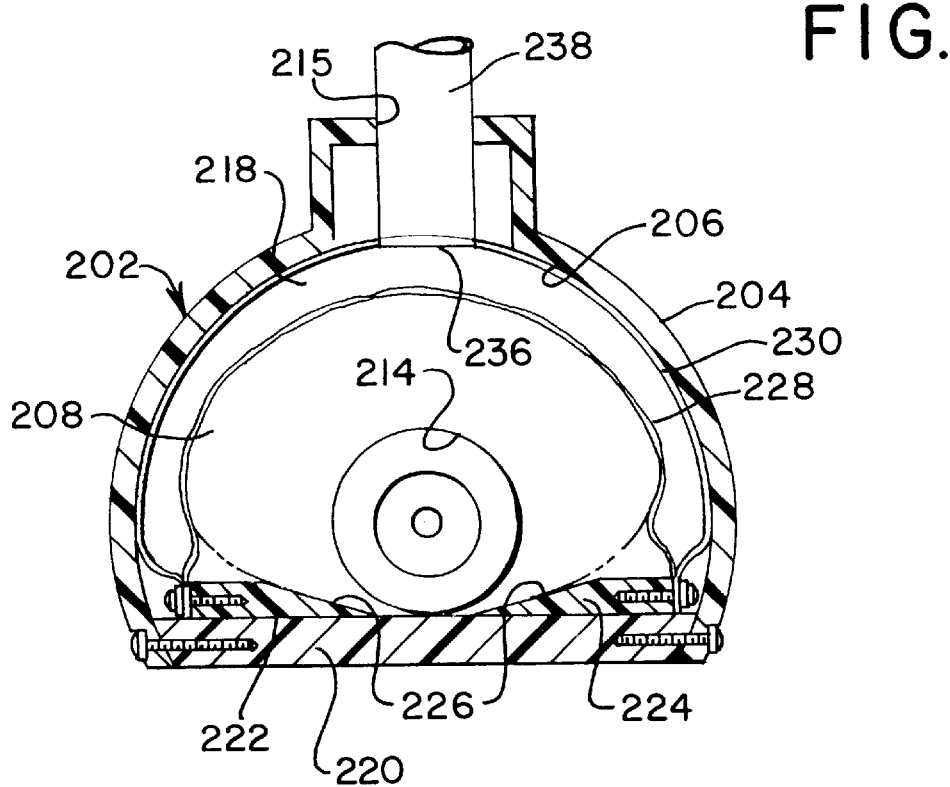
FIG. 22 is a cross-sectional view, showing a systolic phase, taken along lines 21—21 of FIG. 20 and looking in the direction of the arrows.

Referring now to FIGS. 20, 21 and 22 the apparatus according to a sixth embodiment of the present invention, generally designated 200, includes a reduced in height open ended housing 202. The housing includes a substantially D-shaped and lateral cross-section wall 204 to define an internal cavity 206. The housing is complementary formed to nest within the chest cavity to minimize the movement of the heart typically associated with the insertion and retraction of the apparatus. Disposed at one end of the housing is an axial wall 208 formed with an outlet port 210 for connecting to a vacuum source 212. As in the first and second embodiments, an axially adjustable tubular conduit may be slidably received in an opening 214 that is disposed in axial end wall 208. The tubular conduit would be connected to the vacuum source 212 to provide a uniform vacuum securing force to the apex region of the heart.

An inlet port 215 is formed near the apex of wall 204 to provide a convenient interface to an inflation system 216. Fluid communication is provided between inflation system 216 and an inflatable cuff-like envelope 218 by conduit 238.

The base of housing 202 is formed by a relatively flat wall 220. A pair of wedge-shaped base walls 222, 224 are fixedly mounted on the inwardly facing surface of base wall 220. The upper surfaces of walls 222, 224 and the free upper surface of wall 220 provide a slightly concave support surface 226 to closely conform to the overall shape of the posterior, inferior surface of the heart. As in the previous embodiments, the base walls 220, 222, 224, can include a plurality of upper opening bores (not shown in this embodiment for the sake of clarity) that are networked and coupled together in fluid communication to define a vacuum manifold in a manner similar to that described and illustrated with respect to the first two embodiments of the present application.

A first and second end of a fluid-impermeable flexible barrier membrane 218 are connected, preferably by a threaded fastener, to the outer ends of base walls 222, 224. Membrane 218 is in the shape of a truncated cuff and includes an inner wall 228 and an outer wall 230 that are sealed together at their first and second sides 232, 234. The outer sheet 230 of the cuff has an opening 236 that is fluidly connected to conduit 238, which provides fluid communication to drive system 216. It is to be understood that the sides 232, 234 of the cuff-shaped envelope are not connected to housing 202.

Operation of the apparatus according to the sixth embodiment of the present invention proceeds substantially similar to that of the fourth and fifth embodiments. Like the operation of the apparatus according to the first, second and third embodiments of the present invention, membrane 218 is constructed of a material or a combination of materials that do not create a transmural pressure in response to pressure within the cuff envelope. As a result, the pressure applied to the exterior ventricular surface of the heart is essentially the same as the pressure within the internal chamber defined by the inner and outer walls 228, 230 of membrane 218.

Those skilled in the art will appreciate the many benefits and advantages offered by the apparatus of the present invention. An important feature of the present invention comprises the heart support manifold platform that conveniently maintains the heart in secure position during assistance. By taking advantage of the relatively flat posterior, inferior surface, more efficient compression of the ventricular region of the heart is utilized.

Further, because no transmural pressure is created by the membrane during pressurization of the fluid chamber, substantially lower fluid pressures may be utilized to obtain better performing hemodynamics. The corresponding increase in hemodynamic efficiency translates to reduced operating costs and increased safety during the heart assisting procedure.

An additional important advantage offered by the present invention is the relatively small size of the overall apparatus, allowing access into the chest cavity of the individual undergoing the heart assistance procedure. Included in the second embodiment of the invention is a reduced-in-height housing to further reduce the overall profile of the apparatus. Moreover, the D-shaped cross sectional configuration enables positioning of the apparatus around the heart with minimal movement of the heart itself. This is highly advantageous because movement of the heart may cause bending or kinking of many of the vessels emanating from the heart, and, thus, obstructing the flow of blood. Additionally, where, as here, the heart may be in a weakened state such that movement is undesirable.

The device of the present invention can be made in various sizes depending on the size of the person or animal for whom it is to be used on. The device's outer dimensions are sized to fit within the chest cavity of the patient. Typically, for humans, only two or three adult sizes may be required along with one or two pediatric sizes.

Having described the presently preferred exemplary embodiment of apparatus and method and apparatus for assisting a heart to pump blood by applying substantially uniform pressure to at least a portion of the ventricles in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

We claim:

1. A method of assisting a heart to pump blood with a device having a housing that defines an internal chamber, said internal chamber being substantially D-shaped in a lateral cross-section configuration a fluid-impermeable barrier being connected to said housing to divide said D-shaped internal chamber into a first heart receiving chamber and a second pressure fluid receiving chamber, said method comprising the steps of:

placing at least a portion of a heart in said first heart receiving chamber; and applying a uniform fluid pressure to said portion of the heart placed within said first heart receiving chamber by increasing the pressure in said second chamber to force said barrier against a heart wall to apply a substantially uniform pressure to at least a predetermined majority portion of an exterior ventricular surface of the heart.

2. The method according to claim 1, wherein during said applying step, applying a fluid pressure to said second chamber on a first side of said barrier resulting in a substantially equal fluid pressure on an opposite second side of said barrier in said first chamber.

3. The method according to claim 2, further comprising the step of relieving said fluid pressure that is applied to said second chamber to reduce pressure applied to the heart.

4. The method according to claim 3, further comprising the step of cyclicly applying fluid pressure to said second chamber and relieving said fluid pressure that is applied to said second chamber.

5. The method according to claim 2, further comprising the step of applying a vacuum fluid pressure to a part of the heart in said first chamber to maintain the position of said heart within said first chamber.

6. An apparatus for assisting a heart to pump blood comprising:
- a housing defining an internal chamber for receiving a heart, said housing having a fluid conduit to supply pressurizing fluid to said internal chamber of said housing;
- means for applying uniform pressure to a majority portion of an exterior ventricular surface of the heart placed within said internal chamber to substantially uniformly deform said ventricular surface of the heart, said means for applying uniform pressure including a fluid impermeable barrier; and
- a plurality of cords, each of said cords having a first end and a second end, said first end of said cords being connected to said barrier, said second end of said cords being connected to said housing.

7. The apparatus according to claim 6, wherein said barrier is connected to said housing to divide said interior chamber into a first chamber and a second chamber, the ventricular surface of the heart being held in said first chambers and fluid being applied to said second chamber.

8. The apparatus according to claim 11, further comprising a first opening in said housing in fluid communication with said second chamber.

9. The apparatus according to claim 8, further comprising a second opening in said housing to apply a vacuum to said first chamber.

10. The apparatus according to claim 8, further comprising a fluid source delivering an alternating supply and removal of fluid to said second chamber through said first opening.

11. The apparatus according to claim 8, further comprising a second opening in said housing in fluid communication with said first chamber.

12. The apparatus according to claim 11, further comprising a vacuum source in fluid communication with said first chamber through said second opening for holding an apical region of a heart.

13. The apparatus according to claim 6, wherein said barrier is made from polyethylene terephthalate.

14. The apparatus according to claim 6, wherein said barrier is made from polyethylene terephthalate reinforced with a woven material.

15. The apparatus according to claim 6, wherein said barrier is made from an inelastic material.

16. The apparatus according to claim 6, wherein said barrier is made from a material, no transmural pressure is created within said material when said ventricular surface of the heart is substantially uniformly deformed.

17. The apparatus according to claim 6, wherein said cords are made of an inelastic material.

18. The apparatus according to claim 6, wherein said barrier is constructed from respective sheets of a tear resistant material and a fluid impermeable material.

19. The apparatus according to claim 18, wherein said tear resistant material comprises nylon, and said fluid impermeable material comprises polyethylene terephthalate.

20. The apparatus according to claim 6, wherein said means for applying uniform pressure includes an iris that is connected to said housing to form a seal between said housing and the portion of the heart placed within said internal chamber.

21. An apparatus for assisting a heart to pump blood comprising:
- a housing defining an internal chamber for receiving at least a portion of a heart, said housing having an opening, said internal chamber being substantially D-shaped in lateral cross-section;
- a barrier connected to said housing to divide said interior chamber into a first chamber for holding the heart and a second chamber for receiving a pressurized fluid to apply pressure against said portion of said heart; and
- a conduit being received in said opening, said conduit having a first axial end and a second axial end, said second axial end having a cup shape and being disposed in said first chamber.

22. The apparatus according to claim 21, wherein said housing is formed in a substantially cylindrical configuration.

23. The apparatus according to claim 22, further comprising a flexible, perforated net being connected to said cup shaped second axial end of said conduit for supporting an apical portion of the heart received within said first chamber.

24. The apparatus according to claim 23, further comprising a screen disposed between a bottom wall of said cup shaped second axial end of said conduit and said net.

25. The apparatus according to claim 24, wherein said screen is spaced from said net.

26. The apparatus according to claim 21, further comprising a heart support platform disposed in said first chamber to support the flat posterior surface of the heart and secure the heart in a fixed position.

27. The apparatus according to claim 26, wherein said heart platform is formed with a plurality of upwardly opening vacuum ports for drawing the heart flat posterior surface in a secure position against said platform, said ports coupled in fluid communication to define a vacuum manifold disposed downstream of a vacuum source.

28. The apparatus according to claim 27, wherein said vacuum ports receive respective upwardly projecting suction cups for adhering to the heart posterior surface and securing the heart in a fixed position.

29. The apparatus according to claim 21, wherein said barrier is made from a material, no transmural pressure is created within said material.

30. An apparatus for assisting a heart to pump blood comprising:
- a housing defining an internal chamber for receiving a heart, said housing having an opening;
- a barrier connected to said housing to divide said interior chamber into a first chamber for holding the heart and a second chamber;
- a conduit being received in said opening, said conduit having a first axial end and a second axial end, said second axial end having a cup shape and being disposed in said first chamber; and
- a flexible, perforated net being connected to said cup shaped second axial end of said conduit for supporting a heart placed within said first chamber.

31. The apparatus according to claim 30, further comprising a screen disposed between a bottom wall of said cup shaped second axial end of said conduit and said net.

32. The apparatus according to claim 30, further comprising a heart support platform to support the flat posterior surface of the heart and secure the heart in a fixed position.

33. The apparatus according to claim 31, wherein said screen is spaced from said net.

34. The apparatus according to claim 32, wherein said heart platform is formed with a plurality of upwardly opening vacuum ports for drawing the heart flat posterior surface in a secure position against said platform, said ports coupled in fluid communication to define a vacuum manifold disposed downstream of a vacuum source.

35. The apparatus according to claim 34, wherein said vacuum ports receive respective upwardly projecting suction cups for adhering to the heart posterior surface and securing the heart in a fixed position.

36. The apparatus according to claim 30, wherein said barrier is made from a material, no transmural pressure is created within said material.

* * * * *